United States Patent
Yuan et al.

(10) Patent No.: US 11,709,463 B2
(45) Date of Patent: Jul. 25, 2023

(54) CONTROL METHOD BASED ON ADAPTIVE NEURAL NETWORK MODEL FOR DISSOLVED OXYGEN OF AERATION SYSTEM

(71) Applicants: Yancheng Institute Of Technology, Yancheng (CN); YCIT Technology Transfer Center Co., Ltd., Yancheng (CN)

(72) Inventors: Ye Yuan, Yancheng (CN); Linfeng Chen, Yancheng (CN); Cheng Ding, Yancheng (CN); Aijie Wang, Yancheng (CN); Tianming Chen, Yancheng (CN); Yunjiang Yu, Yancheng (CN); Wanxin Yin, Yancheng (CN)

(73) Assignees: Yancheng Institute Of Technology, Yancheng (CN); YCIT Technology Transfer Center Co., Ltd., Yancheng (CN)

( * ) Notice: Subject to any disclaimer, the term of this patent is extended or adjusted under 35 U.S.C. 154(b) by 0 days.

(21) Appl. No.: 17/975,198

(22) Filed: Oct. 27, 2022

(65) Prior Publication Data
US 2023/0047297 A1 Feb. 16, 2023

(51) Int. Cl.
*G05B 13/02* (2006.01)
*G06F 18/2135* (2023.01)
(Continued)

(52) U.S. Cl.
CPC ..... *G05B 13/0285* (2013.01); *G01N 33/1806* (2013.01); *G06F 18/2135* (2023.01); *G06N 7/046* (2013.01)

(58) Field of Classification Search
CPC ............ G05B 13/0285; G06F 18/2135; G01N 33/1806; G06N 7/046
(Continued)

(56) References Cited

U.S. PATENT DOCUMENTS

| | | | | |
|---|---|---|---|---|
| 5,852,817 A | * | 12/1998 | Kano | G05B 13/027 706/903 |
| 2014/0052422 A1 | * | 2/2014 | Wan | C02F 3/006 703/2 |
| 2022/0055929 A1 | * | 2/2022 | Liao | C02F 3/006 |

FOREIGN PATENT DOCUMENTS

| CN | 102122134 A | 7/2011 |
|---|---|---|
| CN | 108536106 A | 9/2018 |

(Continued)

OTHER PUBLICATIONS

Khatri, et al., "Artificial neural network modelling of faecal coliform removal in an intermittent cycle extended aeration system-sequential batch reactor based wastewater treatment plant", Journal of Water Process Engineering 376 (2020) 101477 (Year: 2020).*

(Continued)

*Primary Examiner* — Tsu-Chang Lee
(74) *Attorney, Agent, or Firm* — CBM Patent Consulting, LLC

(57) ABSTRACT

A control method based on an adaptive neural network model for dissolved oxygen of an aeration system includes: obtaining related water quality monitoring data of a sewage treatment plant, and performing data preprocessing on the related water quality monitoring data; performing principal component analysis on the preprocessed related water quality monitoring data and a dissolved oxygen concentration of the aeration system through a principal component analysis method, and determining a water quality parameter with a highest rate of contribution to a principal component; taking the water quality parameter with the highest rate of contribution to the principal component, and predicting a dissolved oxygen concentration of the aeration system; and optimizing a dissolved oxygen predictive value obtained by means of the adaptive neural network model to obtain an optimal regulation value, and performing online regulation on a fuzzy control system of the adaptive neural network model.

8 Claims, 3 Drawing Sheets

(51) Int. Cl.
*G01N 33/18* (2006.01)
*G06N 7/04* (2006.01)

(58) Field of Classification Search
USPC .............................................................. 706/2
See application file for complete search history.

(56) References Cited

FOREIGN PATENT DOCUMENTS

| | | |
|---|---|---|
| CN | 110059824 A | 7/2019 |
| CN | 110378533 A | 10/2019 |

OTHER PUBLICATIONS

Mingzhi, et al., "Control rules of aeration in a submerged biofilm watewater treatment process using fuzzy neural networks", Expert System with Applications 36 (2009) 10428-10437 (Year: 2009).*
Sima Haifeng et al. Intelligent Computing Methods in Classification of Remote Sensing Images, pp. 197-199, Jan. 31, 2018.
Cheng Fengwei et al., Artificial Intelligence Implementation Technology and Development Research, p. 157-158, Mar. 31, 2019.
Li Shaobo et al. Research on Prediction and Simulation of Dissolved Oxygen in Aquaculture Computer Simulation, vol. 32, No. 11, p. 307-310 Nov. 30, 2015.

* cited by examiner

CONTROL METHOD BASED ON ADAPTIVE NEURAL NETWORK MODEL FOR DISSOLVED OXYGEN OF AERATION SYSTEM

CROSS REFERENCES

This application claims priority to Chinese Patent Application Ser. No. CN202111609714.9 filed on 25 Dec. 2021.

TECHNICAL FIELD

The present disclosure provides a control method based on an adaptive neural network model for dissolved oxygen of an aeration system, which belongs to the technical field of system control.

BACKGROUND ART

With the increasingly serious water pollution problem and the national emphasis on the environmental protection industry, sewage treatment has become an important component of municipal construction. For a long time, an activated sludge method is mostly adopted for secondary biological treatment of municipal domestic sewage in China, is a secondary biological treatment process which is the most widely applied to all countries in the world at present, and has the advantages of high treatment capacity, good effluent quality, etc. According to a sewage treatment process through the activated sludge method, sewage is aerated through an air blower, pollutants in the sewage are decomposed, absorbed or adsorbed through a metabolism effect of aerobic microorganisms in the sewage, and finally a water purification process is achieved. The activated sludge method has the advantages of being low in treatment cost, high in efficiency, small in secondary pollution, etc. and is a mainstream sewage treatment manner at present.

The sewage treatment process through the activated sludge method is accompanied by a series of complex biochemical reactions, and an aeration tank is a very important link. According to an aeration system, the dissolved oxygen amount of sewage is adjusted, such that the growth and reproduction requirements of microorganisms are maintained under a proper dissolved oxygen condition, pollutants in the water are removed, and the effluent quality reaches the discharge standard. The dissolved oxygen content is a very important index parameter in the sewage treatment process, and a too high content and a too low content both can cause deterioration of a sludge living environment. However, the aeration system is a complex reaction process with strong coupling, non-linearity and large lag, and a great number of parameters are difficult to measure or cannot be directly measured in the treatment process, such that a control system is low in precision, resulting in the problems of aeration quantity redundancy and large dissolved oxygen fluctuation, the effluent quality is influenced, and a large amount of energy consumption is wasted. The power consumption of the aeration system accounts for greater than 60% of the total power consumption of a sewage treatment plant. According to the present disclosure, dissolved oxygen of an aeration tank in a sewage treatment system is predicted in combination with an adaptive neural network model, such that the measurement precision can be improved, the effluent quality of a sewage treatment plant is improved, and the system energy consumption is reduced.

SUMMARY

The present disclosure provides a control method based on an adaptive neural network model for dissolved oxygen of an aeration system. According to the method, a dissolved oxygen concentration prediction model is established by utilizing water quality parameter data related to an aeration tank provided by a sewage treatment system, and an online regulation method is performed to improve the effluent quality of a sewage treatment plant and reduce the system energy consumption, thereby solving the problem that an existing control method is low in sewage treatment water quality and high in energy consumption. The adopted technical solution is as follows:

According to the present disclosure, water quality parameter data related to the aeration tank provided by the sewage treatment system is utilized, the data is input into the adaptive neural network model for learning after being subjected to data preprocessing, and a prediction result is obtained. Then, an obtained predictive value is optimized and calculated by utilizing a fuzzy algorithm, and online regulation is performed.

Specifically, a control method based on an adaptive neural network model for dissolved oxygen of an aeration system includes:

step 1. monitoring and acquiring water quality data of a sewage treatment plant in real time to obtain related water quality monitoring data, and performing data preprocessing on the related water quality monitoring data;

step 2. performing principal component analysis on the preprocessed related water quality monitoring data and a dissolved oxygen concentration of the aeration system through a principal component analysis method, and determining a water quality parameter with a highest rate of contribution to a principal component in the related water quality monitoring data;

step 3. taking the water quality parameter with the highest rate of contribution to the principal component determined through the principal component analysis method as an input of the adaptive neural network model, and predicting a dissolved oxygen concentration of the aeration system at each moment through the adaptive neural network model; and step 4. optimizing a dissolved oxygen predictive value obtained by means of the adaptive neural network model through a fuzzy algorithm to obtain an optimal regulation value, and performing online regulation on a fuzzy control system of the adaptive neural network model by utilizing the optimal regulation value.

Furthermore, the related water quality monitoring data in step 1 includes a chemical oxygen demand (COD) of input water, a flow (Q) of the input water, and long-term monitoring data of a temperature (T), a pH value, a sludge volume index (SVI), a 30-min settling velocity (SV30), mixed liquor suspended solids (MLSS), suspended solids (SS) and dissolved oxygen (DO) in an aeration reaction tank.

Furthermore, the data preprocessing includes data noise reduction, abnormal data value elimination and data filling.

Furthermore, principal component analysis is performed on the preprocessed related water quality monitoring data according to the following formula:

$$X_{m \times n} = \begin{pmatrix} x_{11} & \cdots & x_{1n} \\ \vdots & \ddots & \vdots \\ x_{m1} & \cdots & x_{mn} \end{pmatrix}$$

$$r_{ij} = \frac{\mathrm{cov}(X_i, X_j)}{\sqrt{\mathrm{var}(X_i)} \cdot \sqrt{\mathrm{var}(X_j)}}$$

-continued
$$\begin{cases} y_1 = C_{11}x_1 + C_{12}x_2 + \ldots + C_{1t}x_t \\ y_t = C_{t1}x_1 + C_{t2}x_2 + \ldots + C_{tt}x_t \end{cases}$$

where $X_{mxn}$ is a sample matrix of the model, m is the number of samples, n is the number of variables, $r_{ij}$ represents a correlation coefficient of $X_i$ and $X_j$, $X_i$ and $X_j$ represent two-dimensional vectors in the sample matrix, var denotes a variance, cov denotes a covariance, $y_1$ represents an index factor $x_1, x_2, \ldots, x_t$ with a maximum variance in all linear combinations satisfying the formula, $y_t$ represents the tth principal component, $C_{11}, C_{12}, \ldots C_{1t}$ represent correlation coefficients of each index $x_t$ of $y_1$, $C_{t1}, C_{t2}, \ldots C_{tt}$ represent correlation coefficients of each index $x_t$ of $y_1$, and $x_1, x_2, \ldots x_t$ represent components in a sample.

Furthermore, a determination criterion for the water quality parameter with the highest rate of contribution to the principal component in the related water quality monitoring data in step 2 is as follows:

the principal component with the cumulative rate of contribution greater than or equal to 85% is selected as the water quality parameter with the highest rate of contribution to the principal component and is taken as the input of the adaptive neural network model to perform dissolved oxygen concentration prediction.

Furthermore, the predicting a dissolved oxygen concentration of the aeration system at each moment through the adaptive neural network model in step 3 includes:

step 301. performing fuzzification processing on the input features, and determining a membership degree function value of each neuron node in the adaptive neural network model;

step 302. calculating an output value of each node of the adaptive neural network model;

step 303. performing normalization processing on a weight of each rule;

step 304. calculating a rule output corresponding to each rule; and step 305. performing defuzzification to obtain an exact amount output.

Furthermore, the detailed process of the predicting a dissolved oxygen concentration of the aeration system at each moment through the adaptive neural network model in step 3 is as follows:

step 301. performing fuzzification processing on input x and y variables, and performing fuzzification operation on each neuron i through a membership degree function to obtain a membership degree of [0, 1], the membership degree being as follows:

$O_{1,i}=\mu_{A_i}(x)$, i=1,2

$O_{1,i}=\mu_{B_{i-2}}(y)$, i=3,4 where x and y are inputs of neuron nodes, and $O_{1,i}$ is a membership degree of a fuzzy set A, $A \in (A_1, A_2, B_1, B_2)$, such that a membership degree function of A is $\mu_A(x)$;

step 302. performing fuzzy set operation on the membership degrees obtained in step 301, and taking the output of the node of the adaptive neural network model as a value obtained by multiplying the membership degree of each neuron:

$O_{2,i}=\mu_A(x)\mu_B(y)$, i=1,2 where the output $O_{2,i}$ of each node corresponds to an incentive intensity shown by the rule;

step 303. performing normalization processing on the weight of each rule obtained in step 302:

$$O_{3,i} = \omega \cdot \frac{\omega_i}{\omega_1 + \omega_2}, i=1,2$$

where $O_{3,i}$ represents the data after normalization processing, and $\omega_i$ is an incentive intensity obtained by a second layer and becomes a rule weight;

step 304. for each rule, calculating a result of the rule, where in layers of the adaptive neural network model, each neuron node has a node membership degree function to calculate a rule output corresponding to each rule:

$O_{4,i}=\overline{\omega}_i f_i=\overline{\omega}_i(p_i x+q_i y+r_i)$ where $O_{4,i}$ represents a rule output, $\overline{\omega}_i$ is the proportion of the corresponding rule weight transmitted from a third layer to a total weight, $\{p_i, q_i, r_i\}$ is a parameter set of nodes of the layer, and parameters of the layer are called conclusion parameters; and step 305. performing defuzzification on the rule outputs obtained in step 304 to obtain an exact output value, and calculating the sum of signals transmitted by all the rules as a node output and a total output of the whole system:

$$O_{5,i} = \sum \overline{\omega}_i \cdot f_i = \frac{\sum \overline{\omega}_i \cdot f_i}{\sum_i \omega_i}$$

where $O_{5,i}$ represents a total output value of the whole system, that is, a predictive value of the adaptive neural network model.

Furthermore, the performing online regulation on a fuzzy control system of the adaptive neural network model by utilizing the optimal regulation value in step 4 includes: performing online regulation on a fuzzy control system of the adaptive neural network model by utilizing a fuzzy proportion integration differentiation (PID) controller, where the fuzzy PID controller includes a PID controller and a fuzzification module, and the fuzzification module continuously monitors a fuzzy relation between an analysis error e and an error change rate $e_c$ of the adaptive neural network model and three parameters of PID during operation, and performs online adjustment on the three parameters of the PID controller according to a fuzzy control rule.

Furthermore, a control system corresponding to the control method for dissolved oxygen of an aeration system includes:

a data processing module which is used for monitoring and acquiring water quality data of the sewage treatment plant in real time to obtain related water quality monitoring data and performing data preprocessing on the related water quality monitoring data;

a data analysis module which is used for performing principal component analysis on the preprocessed related water quality monitoring data and the dissolved oxygen concentrations of the aeration system through the principal component analysis method, and determining the water quality parameter with the highest rate of contribution to the principal component in the related water quality monitoring data;

a neural network model prediction module which is used for taking the water quality parameter with the highest rate of contribution to the principal component determined by the principal component analysis method as the input of the adaptive neural network model, and predicting the dissolved oxygen concentration of the aeration system at each moment through the adaptive neural network model; and an intelligent regulation module which is used for optimizing a dissolved oxygen predictive value obtained by means of the adaptive neural network model through the fuzzy algorithm to obtain the optimal regulation value, and performing online regulation on the fuzzy control system of the adaptive neural network model by utilizing the optimal regulation value.

Furthermore, the monitoring and acquiring water quality data of a sewage treatment plant in real time to obtain related water quality monitoring data in step 1 includes:

setting a preset group time period, the time range of the preset group time period being 30 s to 60 s;

acquiring water quality data in the preset group time period, and determining the number of acquired data of each type of water quality parameter in the current group of water quality data acquired in the preset group time period when the preset group time period is ended, where water quality parameter types contained in the water quality data comprise a chemical oxygen demand of input water, a flow of the input water, and monitoring data of a temperature, a pH value, a sludge volume index, a 30-min settling velocity, mixed liquor suspended solids, suspended solids and dissolved oxygen in an aeration reaction tank.

adjusting the duration of the preset group time period according to the number of the acquired data of each type of water quality parameter until the number is adjusted to a specified data number standard, and determining the corresponding adjusted preset group time period under the condition of satisfying the specified data number standard as a standard group time period, where the specified data number standard is that the number of the acquired data of at least one type of water quality parameter in the current group of water quality data is one, and the number of the acquired data of the other types of water quality parameters in the current group of water quality data is not greater than three at most, when the duration of the preset group time period is adjusted, a single time adjustment amplitude is obtained according to the following formula:

$$\Delta T_z = INT(0.08 \cdot T_0)$$

$$\Delta T_j = \left(1 + \frac{T_1}{T_0}\right) \cdot \frac{1}{k} \cdot \sum_{i=1}^{k} T_i$$

where $\Delta T_z$ represents a single time adjustment amplitude under the condition that the preset group time period needs to be prolonged, $\Delta T_j$ represents a single time adjustment amplitude under the condition that the preset group time period needs to be shortened, INT ( ) denotes a floor function, $T_0$ represents a preset group time period, k represents the number of types of the water quality parameters with greater than three pieces of acquired data in the water quality data acquired in the current preset group time period, $T_i$ represents a data acquisition time interval of the water quality parameters of which the number of the ith acquired data exceeds three in the water quality data acquired in the current preset group time period, $T_1$ represents a data acquisition time interval corresponding to the water quality parameter with the greatest number of the acquired data in the k types of water quality parameters with the number of the acquired data exceeding three;

acquiring the water quality data in real time in each standard group time period, wherein each standard group time period serves as a data acquisition period and corresponds to one group of water quality data, after each group of water quality data is acquired, performing average number processing on each type of water quality parameter containing a plurality of acquired data numbers in each group of water quality data, obtaining a unique water quality parameter corresponding to the water quality parameter containing the plurality of acquired data numbers, and ensuring that each type of water quality parameter only contains one piece of parameter data in each group of water quality data; and taking one group of water quality data of which each processed water quality parameter only contains one piece of parameter data as related water quality monitoring data acquired in the current data acquisition period.

The present disclosure has the beneficial effects:

According to the control method based on an adaptive neural network model for dissolved oxygen of an aeration system provided by the present disclosure, the adaptive neural network model is established by analyzing influence factors of the dissolved oxygen of the sewage treatment aeration reaction tank, the concentration of the dissolved oxygen may be effectively predicted, and the output value is optimized and regulated through the fuzzy control system, such that the dissolved oxygen prediction accuracy in the sewage treatment process of the sewage treatment plant may be effectively improved, thereby effectively improving the adaptive regulation accuracy of the aeration tank control system and improving the effluent quality of the sewage treatment plant to the maximum extent; and moreover, according to the control method based on an adaptive neural network model for dissolved oxygen of an aeration system provided by the present disclosure, on the premise that the effluent quality is effectively improved, the system energy consumption is further reduced to the maximum extent, and energy saving is achieved.

DETAILED DESCRIPTION OF THE EMBODIMENTS

Preferred embodiments of the present disclosure will be described below with reference to the accompanying drawings. It should be understood that the preferred embodiments described herein are only used for describing and explaining the present disclosure but are not intended to limit the present disclosure.

According to the present disclosure, water quality parameter data related to the aeration tank provided by the sewage treatment system is utilized, the data is input into an adaptive neural network model for learning after being subjected to data preprocessing, and a prediction result is obtained. Then, an obtained predictive value is optimized and calculated by utilizing a fuzzy algorithm, and online regulation is performed.

Figure 1:
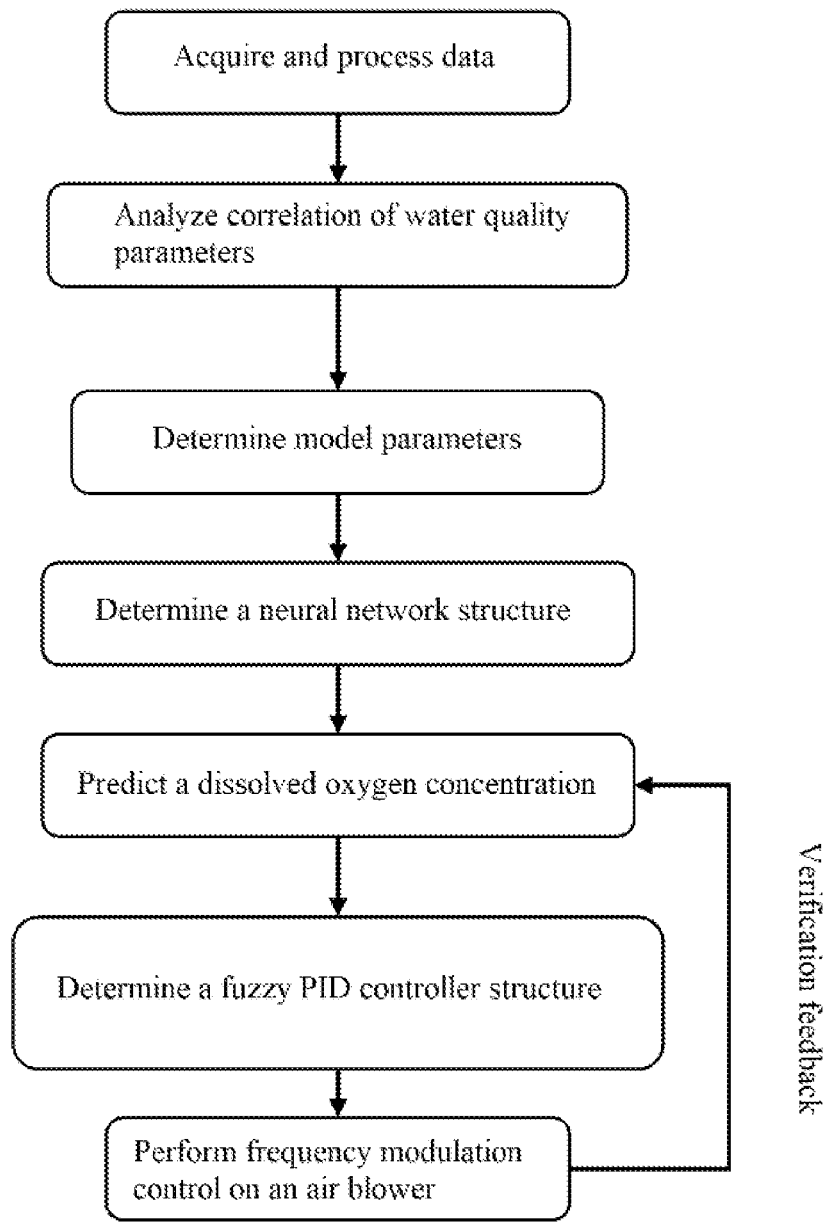
FIG. 1 is a flow diagram of the present disclosure.
Figure 2:
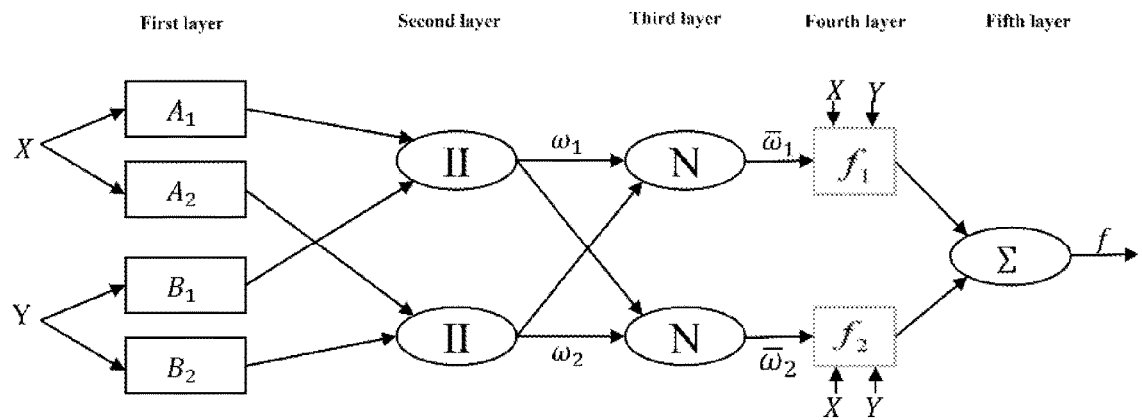
FIG. 2 is a schematic structural diagram of an adaptive neural network of the present disclosure.
Figure 3:
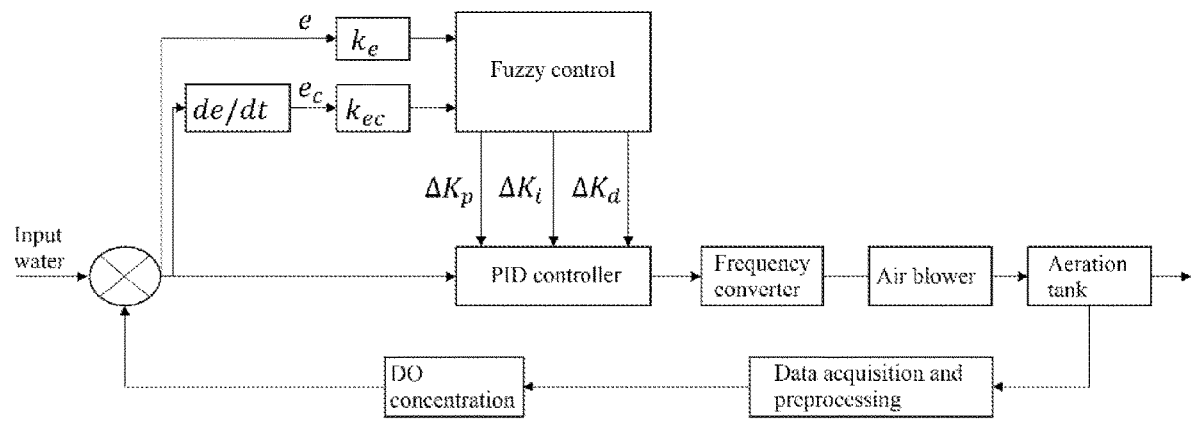
FIG. 3 is a schematic diagram of a fuzzy control system of the present disclosure.
Figure 4:
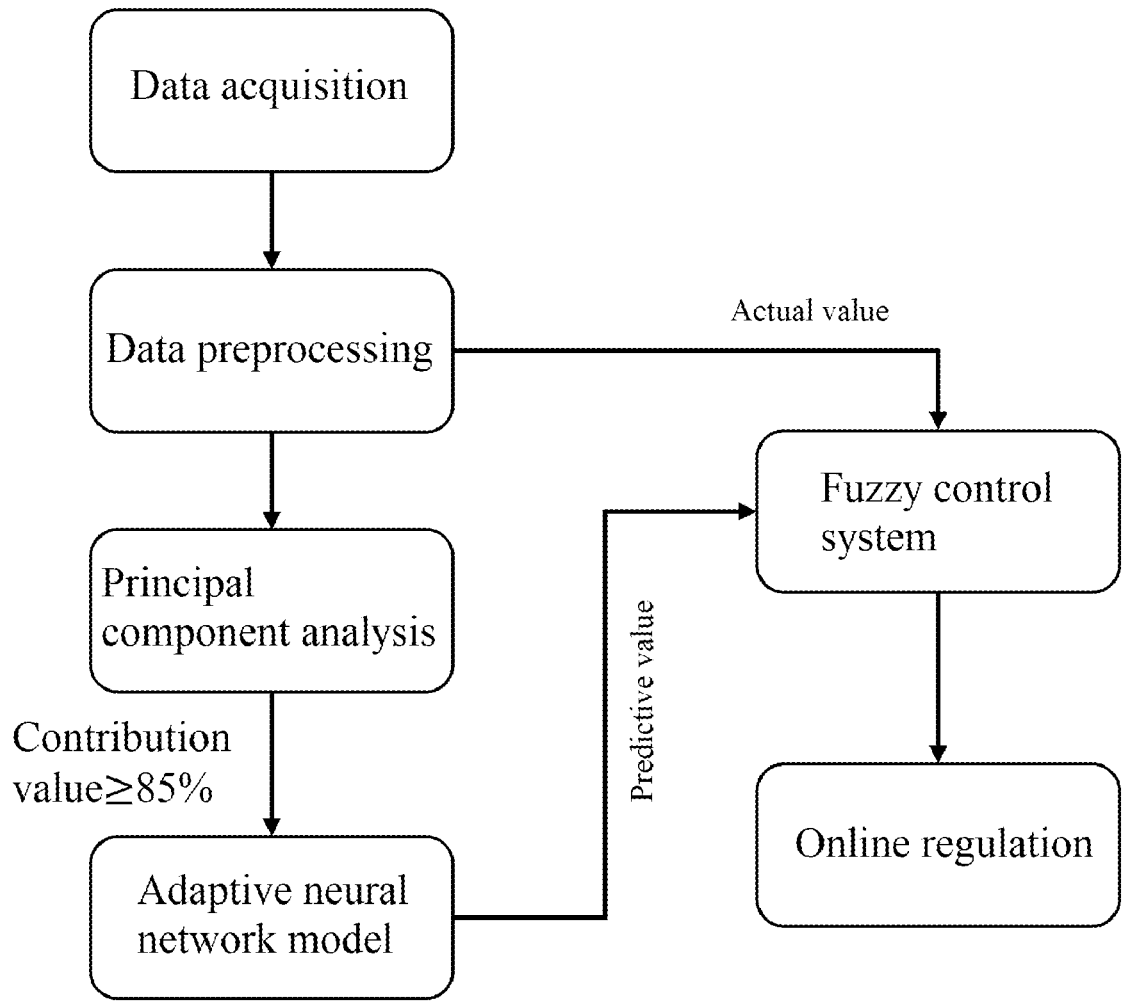
FIG. 4 is a schematic diagram of an implementation of the present disclosure.

A control method based on an adaptive neural network model for dissolved oxygen of an aeration system, as shown in FIG. 1, includes:

step 1. monitor and acquire water quality data of a sewage treatment plant in real time to obtain related water quality monitoring data, and perform data preprocessing on the related water quality monitoring data, where the related water quality monitoring data in step 1 includes a chemical oxygen demand (COD) of input water, a flow (Q) of the input water, and long-term monitoring data of a temperature (T), a pH value, a sludge volume index (SVI), a 30-min settling velocity (SV30), mixed liquor suspended solids (MLSS), suspended solids (SS) and dissolved oxygen (DO) in an aeration reaction tank, and the data preprocessing includes data noise reduction, abnormal data value elimination and data filling.

Step 2. perform principal component analysis on the preprocessed related water quality monitoring data and a dissolved oxygen concentration of the aeration system through a principal component analysis method, and determine a water quality parameter with a highest rate of contribution to a principal component in the related water quality monitoring data. Specifically, principal component analysis is performed on the preprocessed related water quality monitoring data according to the following formula:

$$X_{m \times n} = \begin{pmatrix} x_{11} & \cdots & x_{1n} \\ \vdots & \ddots & \vdots \\ x_{m1} & \cdots & x_{mn} \end{pmatrix}$$

$$r_{ij} = \frac{\text{cov}(X_i, X_j)}{\sqrt{\text{var}(X_i)} \cdot \sqrt{\text{var}(X_j)}}$$

$$\begin{cases} y_1 = C_{11}x_1 + C_{12}x_2 + \ldots + C_{1t}x_t \\ y_t = C_{t1}x_1 + C_{t2}x_2 + \ldots + C_{tt}x_t \end{cases}$$

where $X_{m \times n}$ is a sample matrix of the model, m is the number of samples, n is the number of variables, $r_{ij}$ represents a correlation coefficient of $X_i$ and $X_j$, $X_i$ and $X_j$ represent two-dimensional vectors in the sample matrix, var denotes a variance, cov denotes a covariance, $y_1$ represents an index factor $x_1, x_2, \ldots, x_t$ with a maximum variance in all linear combinations satisfying the formula, $y_t$ represents the tth principal component, $C_{11}, C_{12}, \ldots C_{1t}$ represent correlation coefficients of each index $x_t$ of $y_1$, $C_{t1}, C_{t2}, \ldots C_{tt}$ represent correlation coefficients of each index $x_t$ of $y_1$, and $x_1, x_2, \ldots x_t$ represent components in a sample.

Moreover, a determination criterion for the water quality parameter with the highest rate of contribution to the principal component in the related water quality monitoring data is as follows: the principal component with the cumulative rate of contribution greater than or equal to 85% is selected as the water quality parameter with the highest rate of contribution to the principal component and is taken as the input of the adaptive neural network model to perform dissolved oxygen concentration prediction.

Step 3. take the water quality parameter with the highest rate of contribution to the principal component determined through the principal component analysis method as an input of the adaptive neural network model, and predict a dissolved oxygen concentration of the aeration system at each moment through the adaptive neural network model; and step 4. optimize a dissolved oxygen predictive value obtained by means of the adaptive neural network model through a fuzzy algorithm to obtain an optimal regulation value, and perform online regulation on a fuzzy control system of the adaptive neural network model by utilizing the optimal regulation value. Specifically, online regulation is performed on a fuzzy control system of the adaptive neural network model by utilizing a fuzzy proportion integration differentiation (PID) controller, where the fuzzy PID controller includes a PID controller and a fuzzification module, and the fuzzification module continuously monitors a fuzzy relation between an analysis error e and an error change rate $e_c$ of the adaptive neural network model and three parameters of PID during operation, and performs online adjustment on the three parameters of the PID controller according to a fuzzy control rule.

Specifically, the step of predicting a dissolved oxygen concentration of the aeration system at each moment through the adaptive neural network model in step 3 includes:

step 301. perform fuzzification processing on the input features, and determine a membership degree function value of each neuron node in the adaptive neural network model;

step 302. calculate an output value of each node of the adaptive neural network model;

step 303. perform normalization processing on a weight of each rule;

step 304. calculate a rule output corresponding to each rule; and step 305. perform defuzzification to obtain an exact amount output.

The detailed implementation processes of step 301 to step 305 are as follows:

step 301. perform fuzzification processing on input x and y variables, and perform fuzzification operation on each neuron i through a membership degree function to obtain a membership degree of [0, 1], where the membership degree is as follows:

$$O_{1,i} = \mu_{A_i}(x), \ i=1,2$$

$$O_{1,i} = \mu_{B_{i-2}}(y), \ i=3,4$$

in the formula, x and y are inputs of neuron nodes, and $O_{1,i}$ is a membership degree of a fuzzy set A, A∈(A₁, A₂, B₁, B₂), such that a membership degree function of A is $\mu_A(x)$;

step 302. perform fuzzy set operation on the membership degrees obtained in step 301, and take the output of the node of the adaptive neural network model as a value obtained by multiplying the membership degree of each neuron:

$$O_{2,i} = \mu_A(x)\mu_B(y), \ i=1,2$$

where the output $O_{2,i}$ of each node corresponds to an incentive intensity shown by the rule;

step 303. perform normalization processing on the weight of each rule obtained in step 302:

$$O_{3,i} = \omega \cdot \frac{\omega_i}{\omega_1 + \omega_2}, \ i = 1, 2$$

where $O_{3,i}$ represents the data after normalization processing, and $\omega_i$ is an incentive intensity obtained by a second layer and becomes a rule weight;

step 304. for each rule, calculate a result of the rule, where in layers of the adaptive neural network model, each neuron node has a node membership degree function to calculate a rule output corresponding to each rule:

$$O_{4,i} = \overline{\omega}_i f_i = \overline{\omega}_i (p_i x + q_i y + r_i)$$

in the formula, $O_{4,i}$ represents a rule output, $\overline{\omega}_i$ is the proportion of a corresponding rule weight transmitted from a third layer to a total weight, $\{p_i, q_i, r_i\}$ is a parameter set of nodes of the layer, and parameters of the layer are called conclusion parameters; and step 305. perform defuzzification on the rule outputs obtained in step 304 to obtain an exact output value, and calculate the sum of signals transmitted by all the rules as a node output and a total output of the whole system:

$$O_{5,i} = \sum \overline{\omega}_i \cdot f_i = \frac{\sum \overline{\omega}_i \cdot f_i}{\sum_k \omega_i}$$

where $O_{5,i}$ represents a total output value of the whole system, that is, a predictive value of the adaptive neural network model.

The above-mentioned technical solution has the effects: according to the control method based on an adaptive neural network model for dissolved oxygen of an aeration system provided by the embodiment, the adaptive neural network model is established by analyzing influence factors of the dissolved oxygen of the sewage treatment aeration reaction tank, the concentration of the dissolved oxygen may be effectively predicted, and the output value is optimized and regulated through the fuzzy control system, such that the effluent quality of the sewage treatment plant is improved, and the system energy consumption is reduced.

According to an embodiment of the present disclosure, a control system corresponding to the control method for dissolved oxygen of an aeration system includes:

a data processing module which is used for monitoring and acquiring water quality data of the sewage treatment plant in real time to obtain related water quality monitoring data and performing data preprocessing on the related water quality monitoring data;

a data analysis module which is used for performing principal component analysis on the preprocessed related water quality monitoring data and the dissolved oxygen concentrations of the aeration system through the principal component analysis method, and determining the water quality parameter with the highest rate of contribution to the principal component in the related water quality monitoring data;

a neural network model prediction module which is used for taking the water quality parameter with the highest rate of contribution to the principal component determined through the principal component analysis method as the input of the adaptive neural network model, and predicting the dissolved oxygen concentration of the aeration system at each moment through the adaptive neural network model; and an intelligent regulation module which is used for optimizing a dissolved oxygen predictive value obtained by means of the adaptive neural network model through the fuzzy algorithm to obtain the optimal regulation value, and performing online regulation on the fuzzy control system of the adaptive neural network model by utilizing the optimal regulation value.

The above-mentioned technical solution has the working principle as follows: firstly, the water quality data of the sewage treatment plant is monitored and acquired in real time to obtain the related water quality monitoring data, and data preprocessing is performed on the related water quality monitoring data; then, principal component analysis is performed on the preprocessed related water quality monitoring data and the dissolved oxygen concentration of the aeration system through the principal component analysis method, and the water quality parameter with the highest rate of contribution to the principal component is determined; next, the water quality parameter with the highest rate of contribution to the principal component determined through the principal component analysis method is taken as the input of the adaptive neural network model, and the dissolved oxygen concentration of the aeration system at each moment is predicted through the adaptive neural network model; and finally, a dissolved oxygen predictive value obtained by means of the adaptive neural network model are optimized through the fuzzy algorithm to obtain the optimal regulation value, and online regulation is performed on the fuzzy control system of the adaptive neural network model by utilizing the optimal regulation value.

The above-mentioned technical solution has the effects as follows: the control system corresponding to the control method based on an adaptive neural network model for dissolved oxygen of an aeration system provided by the embodiment is used for executing the control method based on an adaptive neural network model for dissolved oxygen of an aeration system, the adaptive neural network model is established by analyzing influence factors of the dissolved oxygen of the sewage treatment aeration reaction tank, the concentration of the dissolved oxygen may be effectively predicted, and the output value is optimized and regulated through the fuzzy control system, such that the effluent quality of the sewage treatment plant is improved, and the system energy consumption is reduced.

According to an embodiment of the present disclosure, the step of monitoring and acquiring water quality data of a sewage treatment plant in real time to obtain related water quality monitoring data in step 1 includes:

firstly, set a preset group time period, where the time range of the preset group time period is 30 s to 60 s;

secondly, acquire water quality data in the preset group time period, and determine the number of acquired data of each type of water quality parameter in the current group of water quality data acquired in the preset group time period when the preset group time period is ended, where water quality parameter types contained in the water quality data include a chemical oxygen demand of input water, a flow of the input water, and monitoring data of a temperature, a pH value, a sludge volume index, a 30-min settling velocity, mixed liquor suspended solids, suspended solids and dissolved oxygen in an aeration reaction tank;

thirdly, adjust the duration of the preset group time period according to the number of the acquired data of each type of water quality parameter until the number is adjusted to a specified data number standard, and determine the corresponding adjusted preset group time period under the condition of satisfying the specified data number standard as a standard group time period, where the specified data number standard is that the number of the acquired data of at least one type of water quality parameter in the current group of water quality data is one, and the number of the acquired data of the other types of water quality parameters in the current group of water quality data is not greater than three at most, when the duration of the preset group time period is adjusted, a single time adjustment amplitude is obtained according to the following formula:

$$\Delta T_z = INT(0.08 \cdot T_0)$$

$$\Delta T_j = \left(1 + \frac{T_1}{T_0}\right) \cdot \frac{1}{k} \cdot \sum_{i=1}^{k} T_i$$

where $\Delta T_z$ represents a single time adjustment amplitude under the condition that the preset group time period needs to be prolonged, $\Delta T_j$ represents a single time adjustment amplitude under the condition that the preset group time period needs to be shortened, INT ( ) denotes a floor function, $T_0$ represents a preset group time period, n represents the number of types of the water quality parameters with greater than three pieces of acquired data in the water quality data acquired in the current preset group time period, $T_i$ represents a data acquisition time interval of the water quality parameters of which the number of the ith acquired data exceeds three in the water quality data acquired in the current preset group time period, and $T_1$ represents a data acquisition time interval corresponding to the water quality parameter with the greatest number of the acquired data in the n types of water quality parameters with the number of the acquired data exceeding three;

fourthly, acquire the water quality data in real time in each standard group time period, where each standard group time period serves as a data acquisition period and corresponds to one group of water quality data, after each group of water quality data is acquired, perform average number processing on each type of water quality parameter containing a plurality of acquired data numbers in each group of water quality data, obtain a unique water quality parameter corresponding to the water quality parameter containing the plurality of acquired data numbers, and ensure that each type of water quality parameter only contains one piece of parameter data in each group of water quality data; and fifthly, take one group of water quality data of which each processed water quality parameter only contains one piece of parameter data as related water quality monitoring data acquired in the current data acquisition period.

The above-mentioned technical solution has the working principle as follows: firstly, the preset group time period is set, where the time range of the preset group time period is 30 s to 60 s; then, the water quality data in the preset group time period is acquired, and the number of the acquired data of each type of water quality parameter in the current group of water quality data acquired in the preset group time period is determined when the preset group time period is ended, where the water quality parameter types contained in the water quality data include the chemical oxygen demand of the input water, the flow of the input water, and the monitoring data of the temperature, the pH value, the sludge volume index, the 30-min settling velocity, the mixed liquor suspended solids, the suspended solids and the dissolved oxygen in the aeration reaction tank; next, the duration of the preset group time period is adjusted according to the number of the acquired data of each type of water quality parameter until the number is adjusted to a specified data number standard, and the corresponding adjusted preset group time period under the condition of satisfying the specified data number standard is determined as a standard group time period, where the specified data number standard is that the number of the acquired data of at least one type of water quality parameter in the current group of water quality data is one, the number of the acquired data of the other types of water quality parameters in the current group of water quality data is not greater than three at most, when the duration of the preset group time period is adjusted, a single time adjustment amplitude is obtained according to the following formula:

$$\Delta T_z = INT(0.08 \cdot T_0)$$

$$\Delta T_j = \left(1 + \frac{T_1}{T_0}\right) \cdot \frac{1}{k} \cdot \sum_{i=1}^{k} T_i$$

where $\Delta T_z$ represents a single time adjustment amplitude under the condition that the preset group time period needs to be prolonged, $\Delta T_j$ represents a single time adjustment amplitude under the condition that the preset group time period needs to be shortened, INT ( ) denotes a floor function, $T_0$ represents a preset group time period, k represents the number of types of the water quality parameters with greater than three pieces of acquired data in the water quality data acquired in the current preset group time period, $T_i$ represents a data acquisition time interval of the water quality parameters of which the number of the ith acquired data exceeds three in the water quality data acquired in the current preset group time period, and $T_1$ represents a data acquisition time interval corresponding to the water quality parameter with the greatest number of the acquired data in the k types of water quality parameters with the number of the acquired data exceeding three; next, the water quality data are acquired in real time in each standard group time period, each standard group time period serves as one data acquisition period and corresponds to one group of water quality data, after each group of water quality data is acquired, average number processing is performed on each type of water quality parameter containing a plurality of acquired data numbers in each group of water quality data to obtain a unique water quality parameter corresponding to the water quality parameter containing the plurality of acquired data numbers and ensure that each type of water quality parameter only contains one piece of parameter data in each group of water quality data; and finally, one group of water quality data of which each processed water quality parameter only contains one piece of parameter data is taken as related water quality monitoring data acquired in the current data acquisition period.

The above-mentioned technical solution has the effects as follows: since the acquisition frequency and the acquisition period of each water quality parameter acquisition device are inconsistent, the original acquisition data need to be planned and processed in a unified manner, and therefore, the problem that data acquisition batches fail to be determined due to different sequential inputs of the acquired data with different acquisition frequencies in the principal component analysis process, resulting in the accuracy of principal component analysis is reduced is solved. By means of the above-mentioned manner, the water quality data acquired by means of different water quality parameter acquisition frequencies may be subjected to unified processing, and the accuracy of subsequent principal component analysis may be effectively improved; moreover, by means of adjustment of the preset group time period through the above-mentioned manner and the formulas, under the condition that the water quality parameter acquisition accuracy is guaranteed, the accurate standard group time period may be obtained at a fastest speed, and the obtaining speed of the standard group time period is effectively improved; and furthermore, by means of the manner by which the adjustment formula of the preset group time period is combined with the specified data number standard, effective parameter data is reserved to the maximum extent in one group of water quality data under the condition that the acquisition frequency and period of each type of water quality parameter are different, and the accuracy of subsequent principal component analysis is further improved.

Apparently, those skilled in the art can make various modifications and variations to the present disclosure without departing from the spirit and scope of the present disclosure. In this way, if these modifications and variations of the present disclosure fall within the scope of the claims of the present disclosure and their equivalent technologies, the present disclosure is also intended to include these modifications and variations.

What is claimed is:

1. A control method based on an adaptive neural network model for dissolved oxygen of an aeration system, comprising a computer readable medium operable on a computer with memory for the -control method based on the adaptive neural network model for dissolved oxygen of an aeration system, and comprising program instructions for executing the following steps:
   step 1. monitoring and acquiring water quality data of a sewage treatment plant in real time to obtain related water quality monitoring data, and performing data preprocessing on the related water quality monitoring data;
   step 2. performing principal component analysis on the preprocessed related water quality monitoring data and a dissolved oxygen concentration of the aeration system through a principal component analysis method, and determining a water quality parameter with a highest rate of contribution to a principal component in the related water quality monitoring data;
   step 3. taking the water quality parameter with the highest rate of contribution to the principal component determined through the principal component analysis method as an input of the adaptive neural network model, and predicting a dissolved oxygen concentration of the aeration system at each moment through the adaptive neural network model;
   step 4. optimizing a dissolved oxygen predictive value obtained by means of the adaptive neural network model through a fuzzy algorithm to obtain an optimal regulation value, and performing online regulation on a fuzzy control system of the adaptive neural network model by utilizing the optimal regulation value,
   wherein the monitoring and acquiring water quality data of a sewage treatment plant in real time to obtain related water quality monitoring data in step 1 comprises:
   setting a preset group time period, the time range of the preset group time period being 30 s to 60 s;
   acquiring water quality data in the preset group time period, and determining the number of acquired data of each type of water quality parameter in the current group of water quality data acquired in the preset group time period when the preset group time period is ended, wherein water quality parameter types contained in the water quality data comprise a chemical oxygen demand of input water, a flow of the input water, and monitoring data of a temperature, a pH value, a sludge volume index, a 30-min settling velocity, mixed liquor suspended solids, suspended solids and dissolved oxygen in an aeration reaction tank;
   adjusting the duration of the preset group time period according to the number of the acquired data of each type of water quality parameter until the number is adjusted to a specified data number standard, and determining the corresponding adjusted preset group time period under the condition of satisfying the specified data number standard as a standard group time period, wherein the specified data number standard is that the number of the acquired data of at least one type of water quality parameter in the current group of water quality data is one, and the number of the acquired data of the other types of water quality parameters in the current group of water quality data is not greater than three at most, when the duration of the preset group time period is adjusted, a single time adjustment amplitude is obtained according to the following formula:

$$\Delta T_z = INT(0.08 \cdot T_0)$$

$$\Delta T_j = \left(1 + \frac{T_1}{T_0}\right) \cdot \frac{1}{k} \cdot \sum_{i=1}^{k} T_i$$

wherein $\Delta T_z$, represents a single time adjustment amplitude under the condition that the preset group time period needs to be prolonged, $\Delta T_j$, represents a single time adjustment amplitude under the condition that the preset group time period needs to be shortened, INT ( ) denotes a floor function, $T_o$ represents a preset group time period, k represents the number of types of the water quality parameters with greater than three pieces of acquired data in the water quality data acquired in the current preset group time period, $T_i$, represents a data acquisition time interval of the water quality parameters of which the number of the ith acquired data exceeds three in the water quality data acquired in the current preset group time period, and $T_j$ represents a data acquisition time interval corresponding to the water quality parameter with the greatest number of the acquired data in the k types of water quality parameters with the number of the acquired data exceeding three;

acquiring the water quality data in real time in each standard group time period, wherein each standard group time period serves as a data acquisition period and corresponds to one group of water quality data, after each group of water quality data is acquired, performing average number processing on each type of water quality parameter containing a plurality of acquired data numbers in each group of water quality data, obtaining a unique water quality parameter corresponding to the water quality parameter containing the plurality of acquired data numbers, and ensuring that each type of water quality parameter only contains one piece of parameter data in each group of water quality data; and taking one group of water quality data of which each processed water quality parameter only contains one piece of parameter data as related water quality monitoring data acquired in the current data acquisition period; and step 5. the aeration system is controlled by the control method for regulating the dissolved oxygen concentration in a water of the sewage treatment plant.

2. The control method for dissolved oxygen of an aeration system according to claim 1, wherein the data preprocessing in step 1 comprises data noise reduction, abnormal data value elimination and data filling.

3. The control method for dissolved oxygen of an aeration system according to claim 1, wherein principal component analysis is performed on the preprocessed related water quality monitoring data according to the following formula:

$$X_{m\times n} = \begin{pmatrix} x_{11} & \cdots & x_{1n} \\ \vdots & \ddots & \vdots \\ x_{m1} & \cdots & x_{mn} \end{pmatrix}$$

$$r_{ij} = \frac{\text{cov}(X_i, X_j)}{\sqrt{\text{var}(X_i)} \cdot \sqrt{\text{var}(X_j)}}$$

$$\begin{cases} y_1 = C_{11}x_1 + C_{12}x_2 + \ldots + C_{1t}x_t \\ y_t = C_{t1}x_1 + C_{t2}x_2 + \ldots + C_{tt}x_t \end{cases}$$

wherein $X_{m\times n}$ is a sample matrix of the model, m is the number of samples, n is the number of variables, $r_{ij}$ represents a correlation coefficient of $X_i$ and $X_j$, $X_i$ and $X_j$ represent two-dimensional vectors in the sample matrix, var denotes a variance, coy denotes a covariance, $y_1$ represents an index factor $x_1, x_2, \ldots, x_t$ with a maximum variance in all linear combinations satisfying the formula, $y_t$ represents the tth principal component, $C_{11}, C_{12}, \ldots C_{1t}$ represent correlation coefficients of each index $x_t$ of $y_1$, $C_{t1}, C_{t2}, C_{tt}$ represent correlation coefficients of each index $x_t$ of $y_1$, and $x_1, X_2, \ldots x_t$ represent components in a sample.

4. The control method for dissolved oxygen of an aeration system according to claim 1, wherein a determination criterion for the water quality parameter with the highest rate of contribution to the principal component in the related water quality monitoring data in step 2 is as follows:
the principal component with the cumulative rate of contribution greater than or equal to 85% is selected as the water quality parameter with the highest rate of contribution to the principal component and is taken as the input of the adaptive neural network model to perform dissolved oxygen concentration prediction.

5. The control method for dissolved oxygen of an aeration system according to claim 1, wherein the predicting a dissolved oxygen concentration of the aeration system at each moment through the adaptive neural network model in step 3 comprises:
step 301. performing fuzzification processing on input features, and determining a membership degree function value of each neuron node in the adaptive neural network model;
step 302. calculating an output value of each node of the adaptive neural network model;
step 303. performing normalization processing on a weight of each rule;
step 304. calculating a rule output corresponding to each rule; and
step 305. performing defuzzification to obtain an exact amount output.

6. The control method for dissolved oxygen of an aeration system according to claim 5, wherein the detailed process of the predicting a dissolved oxygen concentration of the aeration system at each moment through the adaptive neural network model in step 3 is as follows:
step 301. performing fuzzification processing on input x and y variables, and performing fuzzification operation on each neuron i through a membership degree function to obtain a membership degree of [0, 1], the membership degree being as follows:

$O_{1,i} = \mu_{A_i}(x)$, i=1,2

$O_{1,i} = \mu_{B_{i-2}}(y)$, i=3,4 wherein x and y are inputs of neuron nodes, and $O_{1,i}$ is a membership degree of a fuzzy set A, $A \in (A_1, A_2, B_1, B_2)$, such that a membership degree function of A is $\mu_A(x)$;
step 302. performing fuzzy set operation on the membership degree obtained in step 301, and taking the output of the node of the adaptive neural network model as a value obtained by multiplying the membership degree of each neuron:

$O_{2,i} = \mu_A(x)\mu_B(y)$, i=1,2 wherein the output $O_{2,i}$ of each node corresponds to an incentive intensity shown by the rule;
step 303. performing normalization processing on the weight of each rule obtained in step 302:

$$O_{3,i} = \omega \cdot \frac{\omega_i}{\omega_1 + \omega_2}, i = 1, 2$$

wherein $O_{3,i}$ represents the data after normalization processing, and $\omega_i$ is the incentive intensity obtained by a second layer and becomes a rule weight;
step 304. for each rule, calculating a result of the rule, wherein in layers of the adaptive neural network model, each neuron node has a node membership degree function to calculate a rule output corresponding to each rule:

$O_{4,i} = \overline{\omega}_i f_i = \overline{\omega}_i (p_i x + q_i y + r_i)$ wherein $O_{4,i}$ represents a rule output, $\overline{\omega}_i$ is the proportion of a corresponding rule weight transmitted from a third layer to a total weight, $\{p_i, q_i, r_i\}$ is a parameter set of nodes of the layer, and parameters of the layer are called conclusion parameters; and
step 305. performing defuzzification on the rule output obtained in step 304 to obtain an exact output value, and calculating the sum of signals transmitted by all the rules as a node output and a total output of the whole system:

$$O_{5,i} = \sum \overline{\omega}_i \cdot f_i = \frac{\sum \overline{\omega}_i \cdot f_i}{\sum_i \omega_i}$$

wherein $O_{5,i}$ represents a total output value of the whole system, that is, a predictive value of the adaptive neural network model.

7. The control method for dissolved oxygen of an aeration system according to claim 1, wherein the performing online regulation on a fuzzy control system of the adaptive neural network model by utilizing the optimal regulation value in step 4 comprises: performing online regulation on a fuzzy control system of the adaptive neural network model by utilizing a fuzzy proportion integration differentiation (PID) controller, wherein the fuzzy PID controller comprises a PID controller and a fuzzification module, and the fuzzification module continuously monitors a fuzzy relation between an analysis error e and an error change rate $e_c$ of the adaptive neural network model and three parameters of PID during operation, and performs online adjustment on the three parameters of the PID controller according to a fuzzy control rule.

8. The control method for dissolved oxygen of an aeration system according to claim 1, wherein a control system corresponding to the control method for dissolved oxygen of an aeration system comprises:

- a data processing module which is used for monitoring and acquiring water quality data of the sewage treatment plant in real time to obtain related water quality monitoring data and performing data preprocessing on the related water quality monitoring data;
- a data analysis module which is used for performing principal component analysis on the preprocessed related water quality monitoring data and the dissolved oxygen concentration of the aeration system through the principal component analysis method, and determining the water quality parameter with the highest rate of contribution to the principal component in the related water quality monitoring data;
- a neural network model prediction module which is used for taking the water quality parameter with the highest rate of contribution to the principal component determined through the principal component analysis method as the input of the adaptive neural network model, and predicting the dissolved oxygen concentration of the aeration system at each moment through the adaptive neural network model; and
- an intelligent regulation module which is used for optimizing the dissolved oxygen predictive value obtained by means of the adaptive neural network model through the fuzzy algorithm to obtain the optimal regulation value, and performing online regulation on the fuzzy control system of the adaptive neural network model by utilizing the optimal regulation value.

* * * * *